United States Patent [19]

Vasile

[11] Patent Number: 4,818,229
[45] Date of Patent: Apr. 4, 1989

[54] DENTAL ULTRASONIC ENDODONTIC UNIT

[75] Inventor: Ion Vasile, Miami, Fla.

[73] Assignee: Engler Engineering Corporation, Hialeah, Fla.

[21] Appl. No.: 43,760

[22] Filed: Apr. 29, 1987

[51] Int. Cl.$^4$ ................................................. A61C 1/14
[52] U.S. Cl. .................................... 433/127; 433/119; 433/86; 433/81
[58] Field of Search ............... 433/102, 119, 118, 124, 433/81, 86, 129, 127; 128/24 A

[56] References Cited

U.S. PATENT DOCUMENTS

| | | | |
|---|---|---|---|
| 2,545,521 | 3/1951 | Knapik | 433/147 X |
| 3,589,012 | 6/1971 | Richman | 433/86 |
| 4,229,168 | 10/1980 | Scholz, Jr. | 433/124 |
| 4,505,676 | 3/1985 | Gonser | 433/86 X |
| 4,571,183 | 2/1986 | Nash | 433/118 |
| 4,580,979 | 4/1986 | Leonard | 433/118 X |
| 4,629,426 | 12/1986 | Levy | 433/102 X |
| 4,682,949 | 7/1987 | Wamin | 433/81 |

*Primary Examiner*—Larry Jones
*Attorney, Agent, or Firm*—Browdy and Neimark

[57] ABSTRACT

A readily manipulatable fastening for a dental endodontic file and tip assembly for operation by ultrasonic vibrations. The fastening is compatible with a wide range of handpieces of different domestic and foreign manufacturers of dental instruments, and may be used interchangeably with ultrasonically operated scaling tips of various shapes and configurations, also catheters and other dental cleaning and scraping tools. A simple and rugged two-part unit consisting of a flow-through tip fastened to the outlet end of the vibratory stack and a completely enclosed housing for the outer end of the tip, other than a single small aperture therein, preferably bored at a small obtuse angle to the longitudinal axis of the tip for the shank of the file, permits a rapidly executed secure fastening or release of the shank from between the end of the tip and the internal end wall of the housing. Preferably, the end wall of the housing and the outer end of the tip are specially contoured to provide a large contact area for the fastening, to transmit the vibratory energy from the transducer to the file with maximum effectiveness and accurate control, with minimum possibility of breakage.

13 Claims, 2 Drawing Sheets

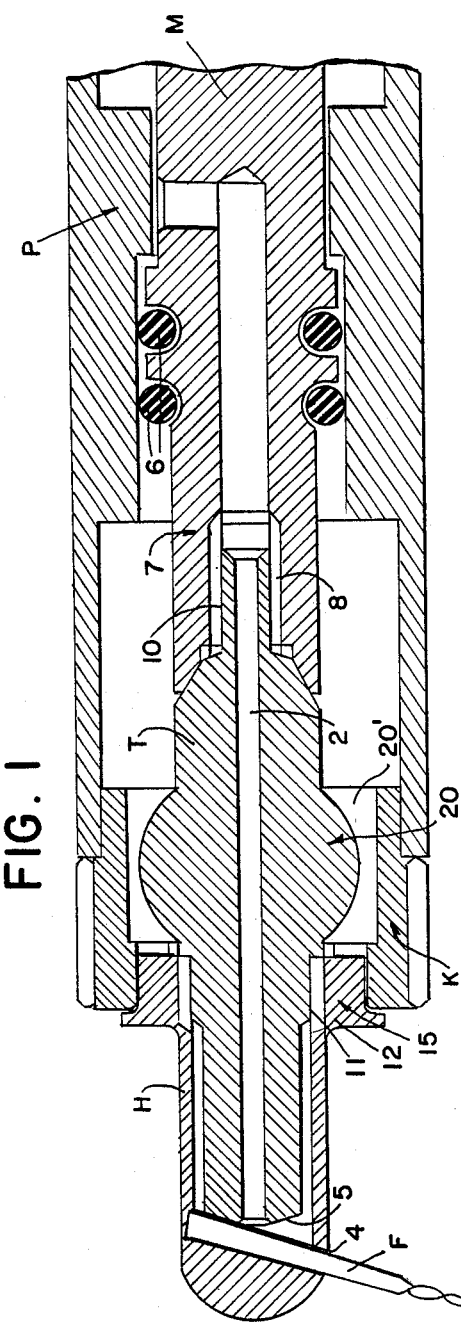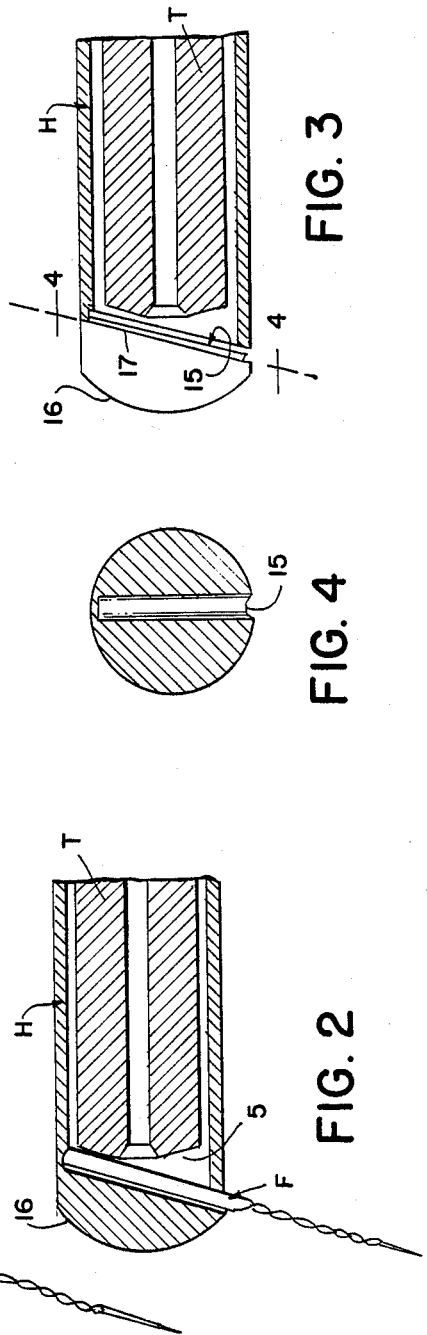

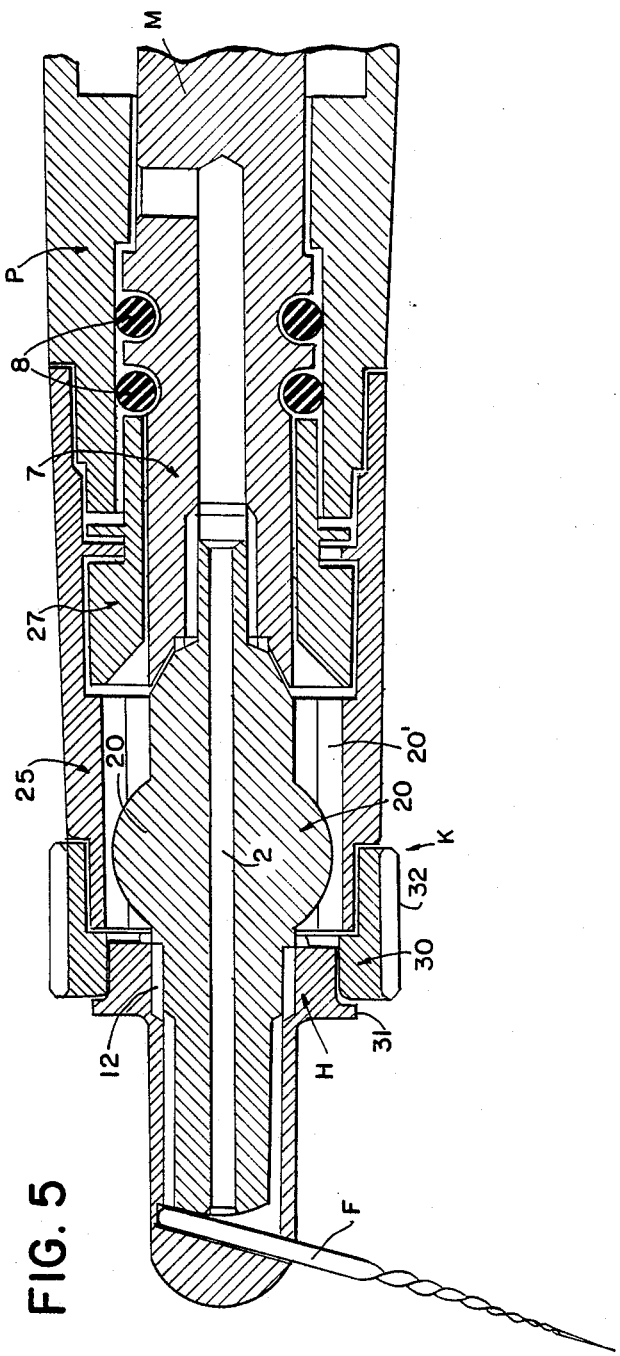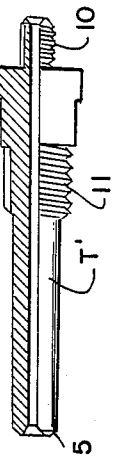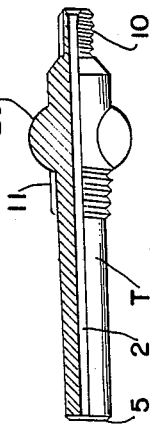

DENTAL ULTRASONIC ENDODONTIC UNIT

BACKGROUND OF THE INVENTION

The instant invention seeks to improve ultrasonic endodontic assemblies, and more particularly to simplify the clamping of the fine endodontic files which are used in root canal work, as described in the following patents: U.S. Pat. Nos. 4,229,168, Scholz, Jr., Oct. 21, 1980, 4,330,278, Martin, May 18, 1982, 4,505,676, Gonser, Mar. 19, 1985, 4,571,183, Nash, Feb. 18, 1986.

SUMMARY OF THE INVENTION

The invention aims to provide a flow-through endodontic tip which may be used interchangeably in handpieces of different manufacturers, both domestic and foreign, for cooperation with a housing of small dimensions for the outer end thereof, which housing is fitted with a single cylindrical opening for loosely accommodating the shank of an endodontic file for secure clamping within the housing between the interior end wall thereof and the outer end of the tip, with enough space surrounding the file to permit the discharge of the liquid in spray form through the opening.

The water or medicaments flowing through the handpiece, which cools the ultrasonic stack, flows through the tip and discharges from the outlet end thereof through the single opening in the housing to flush the matter being removed from the root canal to enable the operator to see the progress of the drilling work which is executed efficiently by virtue of the tight connection between the output of the energizing stack and the shank of the endodontic file.

The fastening and release of the file from said housing requires no extraneous tools and is accomplished by rotation of a keying collar at the outer end of the handpiece which remains in place thereon without affecting the ease of manipulation of the handpiece and the file extending transversely therefrom slightly beyond thereof.

It is an object of the invention to provide a rectilinear tip of simple construction which is rugged, long-lasting, and economical to produce, and which may be easily sterilized.

It is another object of the invention to provide a tip which may be fastened to the output of the energizing stack by the use of diametrally opposed radial ears operated by slotted bushings, or flats operated by end wrenches. Both forms of tips cooperate with a closed housing in accordance with the invention.

Other objects and purposes will appear from the following detailed description of preferred embodiments of the invention in conjunction with the accompanying drawings, wherein FIG. 1 is a longitudinal sectional view illustrating the improved fastening of an endodontic file within a closed housing;

FIG. 2 is a longitudinal sectional view of the end of the instrument shown in FIG. 1, with a specially contoured end wall;

FIG. 3 is a view corresponding to FIG. 2 showing the position of the parts preparatory to the insertion of the file into the housing;

FIG. 4 is a sectional view along line 4—4 of FIG. 3;

FIG. 5 is a longitudinal sectional view of another embodiment of a handpiece with the tip and housing of the invention connected thereto;

FIG. 6 is a longitudinal sectional view of the tip with certain parts in elevation, as shown in FIGS. 1 and 5;

FIG. 7 is a right end view of FIG. 6;

FIG. 8 is a longitudinal sectional view of another embodiment of a tip provided with flats for fastening the inner end of the tip to the outlet of the stack; and FIG. 9 is a left end view of FIG. 8.

In the drawings, FIG. 1 shows a handpiece P of conventional construction enclosing the extending portion of a magnetic transducer M which generates ultrasonic energy, to the outlet end of which may be fastened instruments of all types actuated by vibrational energy of high frequency for cleansing, scraping, drilling, and other functions.

The construction of these instruments is well known in the art, details of which may be found in U.S. Pat. No. 3,589,012, June 29, 1971, as well as in the abovementioned patents, which are illustrative of the prior art.

The tip T may be attached to the outlet of the stack by having the inner end thereof provided with external threads 10 which cooperate with internal threads 8 at the outlet end of the stack. Fluids or medicaments are fed to the handpiece for passage alongside, around and through the stack to cool it, and ultimately through opening 1 to the central channel 2 in the tip for discharge through the opposite end thereof into the housing H and therefrom through the small cylindrical opening 4 in the lateral wall of the housing near its end, through which the shank of the file F is inserted and withdrawn. The shank does not extend from the wall opposite opening 4.

Packing rings 6 serve to restrict the flow of the fluids in the handpiece to the radial passage 1 and the central channel 2 through the stack and the tip.

As described above, when interchangeability of tools is desired, the inner end of the tip T is fastened to the extension 7 of the stack M by means of threads 8 and 10 (FIG. 6). This connection is executed by rotation of the keying bush K which is provided with diametrally opposed radial slots 20' which accommodate the diametrally opposed ears 20 so that clockwise rotation of the bush effects the tight seating of the conical end of the tip into a correspondingly shaped tapered seat at the end of the transducer.

As clearly shown in FIG. 6, external threads 11 are provided on the tip beyond the wings 20 for threaded engagement with internal threads 12 at the open end of the housing H. Longitudinal grooves in the enlarged end 15 of the housing H mesh with cooperating protuberances in the keying bush K so that the limited rotation of the latter controls the relative positioning between the end of the tip and the inner end wall of the housing. This limited rotation of the housing serves to vary the spacing between the end of the tip and the inner end wall to permit the entry of the shank of the file, as shown in FIG. 3, and thereafter upon reverse rotation of the keying bush to reduce this spacing, as shown in FIG. 2, to clamp the file between the tip and the inner wall of the housing.

Preferably, the inner wall of the housing is provided with a groove 15 extending from the outermost portion of opening 4, so that part of the lateral wall of the shank of the file may be seated or nested therein. Also, in supplement to this nesting, the end of the tip at 5 is tapered so that the radial elements on the flaring surface thereof are parallel to the base of the groove 15. Thus, if the axis of the opening 4 in the housing is inclined 100° to the longitudinal axis of the tip to form an obtuse angle of 100°, the end wall 5 of the tip is similarly inclined, so that in the clamped position of the shank of the file, a tight connection is formed between the tip, housing and file therebetween them thereby transmitting effectively the vibrating forces engendered by the transducer.

In operation, fluids emanating from the outer end of the tip discharge through the opening 4 and serve to irrigate the root canal being operated upon and wash away the matter from the source of the operation.

FIG. 5 shows another embodiment of a handpiece wherein a bushing 27 extends beyond the O-rings 8 requiring a larger nose cone 25 around the outer end of the bushing. The nose cone is provided with diametrally opposed slots 20' in engagement with the ears 20 of the tip to effect the connection of the latter to the transducer.

The radial ribs 32 on the exterior of the keying bush K facilitate rotation of the latter and inwardly directed protuberances 30 engage with corresponding external grooves 31 at the enlarged open end of the housing to control the translating movement of the housing relative to the end of the tip, as described above, to effect the clamping and releasing of the file without need of any extranseous tools.

In this embodiment as well, the inner face of the end wall may be grooved, as shown in FIGS. 3, 4 and 5, to increase the extent of clamping areas between the parts to attain the advantages described above.

As alternatives to the ears 20 on the tips which are seated in radial slots 20', the tip T' shown in FIGS. 8 and 9 may be provided with flats 21, for engagement with a suitable end wrench for fastening the tip and the outer end of the transducer. The clamping action between the outer end of the tip, the inner end wall of the housing and the shank of the file therebetween, is the same for either tip as described above.

I claim:

1. In an assembly for operating an endodontic file in a dental handpiece at ultrasonic frequencies,
   (a) a rectilinear tip provided with a central passage for fluids or medicaments adapted to have one end thereof connected to the output end of an ultrasonic vibratory unit within the handpiece, and the other end of the tip extending beyond the free end of said handpiece and having an external thread along an intermediate portion of said tip,
   (b) housing means for entirely covering said tip, said housing means including a housing having a closed outer end and internal threads adjacent to the open end thereof for threaded engagement with said external thread along said intermediate portion of said tip,
   (c) said housing having a single opening in the lateral wall thereof adjacent to its closed end extending transversely to the longitudinal axis of said tip,
   (d) said opening adapted to accommodate loosely the shank of an endodontic file for clamping against the inner wall of the closed end of said housing by the outer end of said tip while leaving room for the discharge of fluid from said passage and through said opening to the remaining portion of said file beyond said housing, and
   (e) said housing means further including rotary means at the end of said handpiece for effecting movement of said housing relative to the outer end of said tip in an axial direction, thereby to selectively clamp and release the shank of the file between the tip and the inner wall of said housing.

2. In an assembly for operating an endodontic file in a dental handpiece at ultrasonic frequencies,
   (a) a rectilinear tip provided with a central passage for fluids or medicaments adapted to have one end thereof connected to the output end of an ultrasonic vibratory unit within the handpiece, and the other end of the tip extending beyond the free end of said handpiece,
   (b) a housing for covering the outer portion of said tip having a closed outer end and internal threads adjacent to the open end thereof for threaded engagement with an intermediate portion of said tip,
   (c) said housing having a single opening in the lateral wall thereof adjacent to its closed end extending at a small obtuse angle transversely to the longitudinal axis of said tip,
   (d) said opening adapted to accommodate loosely the shank of an endodontic file for clamping against the inner wall of the closed end of said housing by the outer end of said tip while leaving room for the discharge of fluid from said passage and through said opening to the remaining portion of said file beyond said housing, and
   (e) a rotary collar keyed to said open end of said housing for imparting limited translatable movement to said housing by slight rotation of said collar, to clamp and release the shank of said file between the end of said tip and the inner face of the end wall of said housing.

3. A device as set forth in claim 2, wherein said obtuse angle is approximately 100°.

4. A device as set forth in claim 3, wherein the outer end of said tip is flared at an angle corresponding to the angularity of said obtuse angle so that substantial line contact is made between the end of the tip and the lateral wall of the shank of the file in the clamped position of the latter.

5. A device as set forth in claim 4, wherein said inner face of said end wall is fitted with a groove parallel to the axis of said opening to seat a portion of the lateral area of the shank of the file in its clamped position.

6. A device as set forth in claim 4, wherein the flared end of said tip is beyond the outlet end of said central passage to permit the discharge of the fluids or medicaments therefrom into said housing and ultimately past the endodontic file projecting therefrom.

7. An assembly for operating an endodontic file, comprising
   (a) a rectilinear tip provided with a central passage for fluids or medicaments;
   (b) threads on one end of said tip for detachably connecting said tip to the output end of an ultrasonic vibratory unit adapted to be contained within a handpiece to which are fed said fluids and power for operating said unit,
   (c) additional external threads at the midportion of said tip,
   (d) a housing for covering the outer portion of said tip having a closed outer end and internal threads adjacent to the open end thereof for engagement with said external threads,
   (e) said housing having a single opening in the lateral wall thereof adjacent to its closed end extending at a small obtuse angle transversely to the longitudinal axis of said tip, (f) said opening adapted to permit insertion of the shank of an endodontic file into said housing for clamping against the inner face of said closed end of said housing by the outer end of said tip, while leaving room for the discharge of fluid from said passage through said opening to the remaining portion of said file beyond said housing, and (g) a rotary collar keyed to said open end of said housing for imparting limited translatable movement to said housing to clamp and release the shank of said file between the end of said tip and the inner face of the end wall of said housing.

8. A device as set forth in claim 7, wherein the outer end of said tip is flared at an angle corresponding to the angularity of said obtuse angle so that line contact is made between the end of the tip and the lateral wall of the shank of the file in the clamped position of the latter.

9. A device as set forth in claim 8, wherein the flared end of said tip is beyond the outlet end of said central passage to permit the discharge of the fluids or medicaments therefrom into said housing and ultimately past the endodontic file projecting therefrom.

10. A device as set forth in claim 7, wherein the inner face of the end wall of said housing is provided with a groove of arcuate cross-section, coincident with the outermost portion of the opening in the lateral wall of the housing.

11. A device as set forth in claim 8, wherein the inner face of the end wall of said housing is provided with a groove of arcuate cross-section, coincident with the outermost portion of the opening in the lateral wall of the housing.

12. A device as set forth in claim 7, including a rotary bushing at the outer end of said handpiece in keying engagement with a portion of said tip to rotate said first-mentioned threads into said detachable connection with said vibratory unit.

13. A device as set forth in claim 12, including a rotary sleeve beyond and adjacent to said rotary bushing at the open end of said housing for controlling the spacing between the outer end of said tip and the inner face of the closed housing.

* * * * *